US009884014B2

(12) United States Patent
Venkatesh

(10) Patent No.: US 9,884,014 B2
(45) Date of Patent: *Feb. 6, 2018

(54) TASTE-MASKED PHARMACEUTICAL COMPOSITIONS

(75) Inventor: Gopi M. Venkatesh, Vandalia, OH (US)

(73) Assignee: ADARE PHARMACEUTICALS, INC., Lawrenceville, NJ (US)

(*) Notice: Subject to any disclaimer, the term of this patent is extended or adjusted under 35 U.S.C. 154(b) by 1325 days.

This patent is subject to a terminal disclaimer.

(21) Appl. No.: 11/248,596

(22) Filed: Oct. 12, 2005

(65) Prior Publication Data
US 2006/0078614 A1   Apr. 13, 2006

Related U.S. Application Data

(60) Provisional application No. 60/617,737, filed on Oct. 12, 2004.

(51) Int. Cl.
A61K 9/00     (2006.01)
A61K 9/20     (2006.01)

(52) U.S. Cl.
CPC .......... A61K 9/0056 (2013.01); A61K 9/2077 (2013.01)

(58) Field of Classification Search
CPC .............................. A61K 9/0056; A61K 9/2077
(Continued)

(56) References Cited

U.S. PATENT DOCUMENTS 3,184,386 A   5/1965   Stephenson
3,558,768 A   1/1971   Klippel
(Continued)

FOREIGN PATENT DOCUMENTS

EP   0052492 B1   2/1984
EP   0166440 A2   1/1986
(Continued)

OTHER PUBLICATIONS

Tirkkonen S., et al., "Enhancement of drug release from ethylcellulose microcapsules using solid sodium chloride in the wall," International Journal of Phrmaceutics, No. 88, pp. 39-51 (1992).
(Continued)

Primary Examiner — Rachael E Bredefeld
(74) Attorney, Agent, or Firm — Cooley LLP

(57) ABSTRACT

There is provided a method for preparing an orally disintegrating tablet (ODT) composition comprising microparticles of one or more taste-masked active pharmaceutical ingredient(s), rapidly-dispersing microgranules, and other optional, pharmaceutically acceptable excipients wherein the ODT disintegrates on contact with saliva in the buccal cavity in about 60 seconds forming a smooth, easy-to-swallow suspension. Furthermore, the microparticles (crystals, granules, beads or pellets containing the active) applied with a taste-masking membrane comprising a combination of water-insoluble and gastrosoluble polymers release not less than about 60% of the dose is in the stomach in about 30 minutes, thus maximizing the probability of achieving bioequivalence to the reference IR product having rapid onset of action (short $T_{max}$). A process for preparing such compositions for oral administration using conventional fluid-bed equipment and rotary tablet press is also disclosed.

27 Claims, 4 Drawing Sheets

(58) Field of Classification Search
USPC .......................................................... 424/470
See application file for complete search history.

(56) References Cited

U.S. PATENT DOCUMENTS

| | | |
|---|---|---|
| 3,885,026 A | 5/1975 | Heinemann et al. |
| 4,078,051 A | 3/1978 | Pomot et al. |
| 4,138,475 A | 2/1979 | McAinsh et al. |
| 4,248,857 A | 2/1981 | DeNeale et al. |
| 4,292,017 A | 9/1981 | Doepel |
| 4,305,502 A | 12/1981 | Gregory et al. |
| 4,369,172 A | 1/1983 | Schor et al. |
| 4,371,516 A | 2/1983 | Gregory et al. |
| 4,389,330 A | 6/1983 | Tice et al. |
| 4,389,393 A | 6/1983 | Schor et al. |
| 4,542,042 A | 9/1985 | Samejima et al. |
| 4,556,678 A | 12/1985 | Hsiao |
| 4,587,118 A | 5/1986 | Hsiao |
| 4,628,098 A | 12/1986 | Nohara et al. |
| 4,661,647 A | 4/1987 | Serpelloni et al. |
| 4,670,459 A | 6/1987 | Sjoerdsma |
| 4,689,333 A | 8/1987 | Nohara et al. |
| 4,698,101 A | 10/1987 | Koivurinta |
| 4,708,867 A | 11/1987 | Hsiao |
| 4,713,248 A | 12/1987 | Kjornaes et al. |
| 4,716,041 A | 12/1987 | Kjornaes et al. |
| 4,728,512 A | 3/1988 | Mehta et al. |
| 4,743,248 A | 5/1988 | Bartoo et al. |
| 4,752,470 A | 6/1988 | Mehta |
| 4,757,090 A | 7/1988 | Salpekar et al. |
| 4,760,093 A | 7/1988 | Blank et al. |
| 4,780,318 A | 10/1988 | Appelgren et al. |
| 4,786,508 A | 11/1988 | Ghebre-Sellassie et al. |
| 4,800,087 A | 1/1989 | Mehta |
| 4,803,213 A | 2/1989 | Lida et al. |
| 4,824,675 A | 4/1989 | Wong et al. |
| 4,832,880 A | 5/1989 | Staniforth |
| 4,840,799 A | 6/1989 | Appelgren et al. |
| 4,851,226 A | 7/1989 | Julian et al. |
| 4,851,229 A | 7/1989 | Magruder et al. |
| 4,863,742 A | 9/1989 | Panoz et al. |
| 4,871,549 A | 10/1989 | Ueda et al. |
| 4,874,613 A | 10/1989 | Hsiao |
| 4,886,669 A | 12/1989 | Ventouras |
| 4,892,741 A | 1/1990 | Ohm et al. |
| 4,894,240 A | 1/1990 | Geoghegan et al. |
| 4,898,737 A | 2/1990 | Panoz et al. |
| 4,915,949 A | 4/1990 | Wong et al. |
| 4,938,968 A | 7/1990 | Mehta |
| 4,946,684 A | 8/1990 | Blank et al. |
| 4,957,745 A | 9/1990 | Jonsson et al. |
| 4,968,508 A | 11/1990 | Oren et al. |
| 4,971,805 A | 11/1990 | Kitanishi et al. |
| 4,983,401 A | 1/1991 | Eichel et al. |
| 5,006,345 A | 4/1991 | Lang |
| 5,011,692 A | 4/1991 | Fujioka et al. |
| 5,013,557 A | 5/1991 | Tai |
| 5,013,743 A | 5/1991 | Iwahi et al. |
| 5,017,122 A | 5/1991 | Staniforth |
| 5,017,381 A | 5/1991 | Maruyama et al. |
| 5,026,559 A | 6/1991 | Eichel et al. |
| 5,026,560 A | 6/1991 | Makino et al. |
| 5,039,540 A | 8/1991 | Ecanow |
| 5,045,321 A | 9/1991 | Makino et al. |
| 5,073,374 A | 12/1991 | McCarty |
| 5,075,114 A | 12/1991 | Roche |
| 5,079,018 A | 1/1992 | Ecanow |
| 5,082,669 A | 1/1992 | Shirai et al. |
| 5,084,278 A | 1/1992 | Mehta |
| 5,093,132 A | 3/1992 | Makino et al. |
| 5,104,648 A | 4/1992 | Denton et al. |
| 5,112,616 A | 5/1992 | McCarty |
| 5,133,974 A | 7/1992 | Paradissis et al. |
| 5,137,733 A | 8/1992 | Noda et al. |
| 5,149,542 A | 9/1992 | Valducci |
| 5,160,680 A | 11/1992 | Serpelloni et al. |
| 5,169,640 A | 12/1992 | France et al. |
| 5,178,878 A | 1/1993 | Wehling et al. |
| 5,204,121 A | 4/1993 | Bucheler et al. |
| 5,211,957 A | 5/1993 | Hagemann et al. |
| 5,213,808 A | 5/1993 | Bar-Shalom et al. |
| 5,229,131 A | 7/1993 | Amidon et al. |
| 5,229,135 A | 7/1993 | Philippon et al. |
| 5,238,686 A | 8/1993 | Eichel et al. |
| 5,252,337 A | 10/1993 | Powell |
| 5,256,699 A | 10/1993 | Murphy et al. |
| 5,260,068 A | 11/1993 | Chen |
| 5,260,069 A | 11/1993 | Chen |
| 5,275,827 A | 1/1994 | Spinelli et al. |
| 5,376,384 A | 12/1994 | Eichel et al. |
| 5,409,711 A | 4/1995 | Mapelli et al. |
| 5,433,959 A | 7/1995 | Makino et al. |
| 5,439,689 A | 8/1995 | Hendrickson et al. |
| 5,445,829 A | 8/1995 | Paradissis et al. |
| 5,464,632 A | 11/1995 | Cousin et al. |
| 5,466,464 A | 11/1995 | Masaki et al. |
| 5,470,584 A | 11/1995 | Hendrickson et al. |
| 5,472,708 A | 12/1995 | Chen |
| 5,478,573 A | 12/1995 | Eichel et al. |
| 5,489,436 A | 2/1996 | Hoy et al. |
| 5,501,861 A | 3/1996 | Makino et al. |
| 5,506,345 A | 4/1996 | Riley et al. |
| 5,508,040 A | 4/1996 | Chen |
| 5,529,790 A | 6/1996 | Eichel et al. |
| 5,536,507 A | 7/1996 | Abramowitz et al. |
| 5,567,441 A | 10/1996 | Chen |
| 5,576,014 A | 11/1996 | Mizumoto et al. |
| 5,609,883 A | 3/1997 | Valentine et al. |
| 5,612,059 A | 3/1997 | Cardinal et al. |
| 5,616,345 A | 4/1997 | Geoghegan et al. |
| 5,629,017 A | 5/1997 | Pozzi et al. |
| 5,639,475 A | 6/1997 | Bettman et al. |
| 5,643,630 A | 7/1997 | Hinzpeter et al. |
| 5,700,492 A | 12/1997 | Morimoto et al. |
| 5,720,974 A | 2/1998 | Makino et al. |
| 5,738,875 A | 4/1998 | Yarwood et al. |
| 5,747,068 A | 5/1998 | Mendizabal |
| 5,762,961 A | 6/1998 | Roser et al. |
| 5,788,987 A | 8/1998 | Busetti et al. |
| 5,807,577 A | 9/1998 | Ouali |
| 5,837,284 A | 11/1998 | Mehta et al. |
| 5,837,285 A | 11/1998 | Nakamichi et al. |
| 5,837,379 A | 11/1998 | Chen et al. |
| 5,840,329 A | 11/1998 | Bai |
| 5,876,759 A | 3/1999 | Gowan, Jr. |
| 5,891,474 A | 4/1999 | Busetti et al. |
| 5,900,252 A | 5/1999 | Calanchi et al. |
| 5,908,638 A | 6/1999 | Huber et al. |
| 5,968,554 A | 10/1999 | Beiman et al. |
| 6,024,981 A | 2/2000 | Khankari et al. |
| 6,024,982 A | 2/2000 | Oshlack et al. |
| 6,033,687 A | 3/2000 | Heinicke et al. |
| 6,039,979 A | 3/2000 | Gendrot et al. |
| 6,096,340 A | 8/2000 | Chen et al. |
| 6,099,859 A | 8/2000 | Cheng et al. |
| 6,099,863 A | 8/2000 | Gilis et al. |
| 6,099,865 A | 8/2000 | Augello et al. |
| 6,103,263 A | 8/2000 | Lee et al. |
| 6,106,861 A | 8/2000 | Chaveau et al. |
| 6,106,862 A | 8/2000 | Chen et al. |
| 6,123,962 A | 9/2000 | Makino et al. |
| 6,129,933 A | 10/2000 | Oshlack et al. |
| 6,136,345 A | 10/2000 | Grimmett et al. |
| 6,139,865 A | 10/2000 | Friend et al. |
| 6,139,877 A | 10/2000 | Debregeas et al. |
| 6,153,220 A | 11/2000 | Cumming et al. |
| 6,162,463 A | 12/2000 | Lippa |
| 6,169,105 B1 | 1/2001 | Wong et al. |
| 6,183,776 B1 | 2/2001 | Depui et al. |
| 6,190,692 B1 | 2/2001 | Busetti et al. |
| 6,221,392 B1 | 4/2001 | Khankari et al. |
| 6,221,402 B1 | 4/2001 | Itoh et al. |
| 6,228,398 B1 | 5/2001 | Devane et al. |
| 6,269,615 B1 | 8/2001 | Amborn et al. |

(56) References Cited

U.S. PATENT DOCUMENTS

| | | |
|---|---|---|
| 6,287,599 B1 | 9/2001 | Burnside et al. |
| 6,316,029 B1 | 11/2001 | Jain et al. |
| 6,328,994 B1 | 12/2001 | Shimizu et al. |
| 6,344,215 B1 | 2/2002 | Bettman et al. |
| 6,350,470 B1 | 2/2002 | Pather et al. |
| 6,350,471 B1 | 2/2002 | Seth |
| 6,365,182 B1* | 4/2002 | Khankari et al. ............ 424/466 |
| 6,368,625 B1 | 4/2002 | Siebert et al. |
| 6,368,628 B1 | 4/2002 | Seth |
| 6,372,253 B1 | 4/2002 | Daggy et al. |
| 6,391,335 B1 | 5/2002 | Pather et al. |
| 6,413,549 B2 | 7/2002 | Green et al. |
| 6,420,473 B1 | 7/2002 | Ramireddy et al. |
| 6,432,534 B1 | 8/2002 | Hayakawa et al. |
| 6,465,009 B1* | 10/2002 | Liu et al. ................... 424/464 |
| 6,465,010 B1 | 10/2002 | Lagoviyer et al. |
| 6,495,160 B2 | 12/2002 | Esposito et al. |
| 6,500,454 B1 | 12/2002 | Percel et al. |
| 6,500,457 B1 | 12/2002 | Midha et al. |
| 6,509,036 B2 | 1/2003 | Pather et al. |
| 6,531,152 B1 | 3/2003 | Lerner et al. |
| 6,551,617 B1 | 4/2003 | Corbo et al. |
| 6,579,535 B2 | 6/2003 | Valentine et al. |
| 6,596,311 B1 | 7/2003 | Dobetti |
| 6,602,521 B1 | 8/2003 | Ting et al. |
| 6,627,223 B2 | 9/2003 | Percel et al. |
| 6,641,838 B2 | 11/2003 | Pather et al. |
| 6,660,382 B2 | 12/2003 | Nouri et al. |
| 6,663,888 B2 | 12/2003 | Percel et al. |
| 6,663,893 B2 | 12/2003 | Corbo et al. |
| 6,740,341 B1 | 5/2004 | Holt et al. |
| 6,897,205 B2* | 5/2005 | Beckert et al. ............ 514/159 |
| 7,048,945 B2 | 5/2006 | Percel et al. |
| 8,071,128 B2 | 12/2011 | Ohta et al. |
| 2001/0007680 A1 | 7/2001 | Kolter et al. |
| 2001/0014340 A1* | 8/2001 | Ohta et al. ............... 424/400 |
| 2001/0046964 A1 | 11/2001 | Percel et al. |
| 2002/0054907 A1 | 5/2002 | Devane et al. |
| 2002/0077348 A1 | 6/2002 | Dean et al. |
| 2002/0142034 A1 | 10/2002 | Shimizu et al. |
| 2002/0187190 A1 | 12/2002 | Cade et al. |
| 2003/0064108 A1 | 4/2003 | Lukas et al. |
| 2003/0096791 A1 | 5/2003 | Gupte et al. |
| 2003/0113374 A1 | 6/2003 | Percel et al. |
| 2003/0134884 A1 | 7/2003 | Hazama et al. |
| 2003/0157173 A1 | 8/2003 | Percel et al. |
| 2003/0161888 A1 | 8/2003 | Fernandez et al. |
| 2003/0215500 A1 | 11/2003 | Ohta et al. |
| 2004/0047906 A1 | 3/2004 | Percel et al. |
| 2004/0121010 A1 | 6/2004 | Hirsh et al. |
| 2004/0122106 A1 | 6/2004 | Ohta et al. |
| 2004/0126427 A1 | 7/2004 | Venkatesh et al. |
| 2004/0131682 A1 | 7/2004 | Percel et al. |
| 2004/0137156 A1 | 7/2004 | Lee et al. |
| 2004/0242536 A1 | 12/2004 | Khoo et al. |
| 2005/0025824 A1 | 2/2005 | Percel et al. |
| 2005/0118268 A1 | 6/2005 | Percel et al. |
| 2005/0152974 A1 | 7/2005 | Boehm et al. |
| 2005/0232988 A1 | 10/2005 | Venkatesh et al. |
| 2005/0269722 A1 | 12/2005 | De Luigi Brushci et al. |
| 2006/0057199 A1 | 3/2006 | Venkatesh et al. |
| 2006/0078614 A1 | 4/2006 | Venkatesh |
| 2006/0105038 A1 | 5/2006 | Lai et al. |
| 2006/0105039 A1 | 5/2006 | Lai et al. |
| 2006/0121112 A1 | 6/2006 | Jenkins et al. |
| 2006/0233892 A1 | 10/2006 | Hendrix |
| 2006/0246134 A1 | 11/2006 | Venkatesh |
| 2006/0269607 A1 | 11/2006 | Percel et al. |
| 2007/0264358 A1 | 11/2007 | Wittlin |
| 2008/0069878 A1 | 3/2008 | Venkatesh et al. |
| 2009/0263480 A1 | 10/2009 | Lai et al. |
| 2011/0212171 A1 | 9/2011 | Venkatesh et al. |
| 2012/0128771 A1 | 5/2012 | Venkatesh |
| 2012/0135076 A1 | 5/2012 | Ohta et al. |

FOREIGN PATENT DOCUMENTS

| | | |
|---|---|---|
| EP | 0239361 A1 | 9/1987 |
| EP | 0349103 A1 | 1/1990 |
| EP | 0357369 A2 | 3/1990 |
| EP | 0391518 A2 | 10/1990 |
| EP | 0431877 A1 | 6/1991 |
| EP | 0453001 A1 | 10/1991 |
| EP | 0516345 A1 | 12/1992 |
| EP | 0538034 A1 | 4/1993 |
| EP | 0553777 A2 | 8/1993 |
| EP | 065826 A1 | 5/1995 |
| EP | 0721777 A2 | 7/1996 |
| EP | 0815931 A1 | 1/1998 |
| EP | 0294493 A1 | 12/1998 |
| EP | 0914818 A1 | 5/1999 |
| EP | 0914823 | 5/1999 |
| EP | 1010423 A2 | 6/2000 |
| EP | 0582396 B1 | 1/2001 |
| EP | 1070497 A1 | 1/2001 |
| EP | 1072257 A1 | 1/2001 |
| EP | 1157690 A1 | 11/2001 |
| EP | 1156786 B1 | 3/2003 |
| EP | 1366759 A1 | 12/2003 |
| EP | 09141823 B1 | 12/2004 |
| EP | 2319498 A1 | 5/2011 |
| FR | 2679451 A1 | 1/1993 |
| FR | 2766089 A1 | 1/1999 |
| FR | 2778848 A1 | 11/1999 |
| GB | 2053787 A | 2/1981 |
| GB | 8824392.8 | 9/1989 |
| GB | 2224207 A | 5/1990 |
| JP | 49-69819 | 7/1974 |
| JP | S5-129224 A | 10/1980 |
| JP | S6-014098 A | 10/1981 |
| JP | 61-143316 A | 7/1986 |
| JP | 62-61916 A | 3/1987 |
| JP | 62-50445 B2 | 10/1987 |
| JP | 62-242616 | 10/1987 |
| JP | 62-246513 A | 10/1987 |
| JP | 62-252723 A | 11/1987 |
| JP | 63-162619 A | 7/1988 |
| JP | 63-270624 A | 11/1988 |
| JP | 1-503385 A | 11/1989 |
| JP | 1-313420 A | 12/1989 |
| JP | 2-500747 A | 3/1990 |
| JP | 2-164824 A | 6/1990 |
| JP | 2-172918 A | 7/1990 |
| JP | 2-289512 A | 11/1990 |
| JP | 3-240724 A | 10/1991 |
| JP | 4-224517 A | 8/1992 |
| JP | 5-241054 A | 10/1993 |
| JP | 5-310558 A | 11/1993 |
| JP | 6-53658 B2 | 7/1994 |
| JP | 6-321790 A | 11/1994 |
| JP | 7-69889 A | 3/1995 |
| JP | 7-124231 A | 5/1995 |
| JP | 8-503482 A | 4/1996 |
| JP | 8-175978 A | 7/1996 |
| JP | 2002-154948 A | 5/2002 |
| JP | 2003-522141 A | 7/2003 |
| JP | 2005-508922 A | 4/2005 |
| NZ | 550608 A | 11/2005 |
| NZ | 554346 A | 5/2006 |
| WO | WO 88/08703 A1 | 11/1988 |
| WO | WO 92/10173 A1 | 6/1992 |
| WO | WO 93/00097 A1 | 1/1993 |
| WO | WO 93/12769 A1 | 7/1993 |
| WO | WO 93/13758 A1 | 7/1993 |
| WO | WO 93/15724 A1 | 8/1993 |
| WO | WO 94/08576 A1 | 4/1994 |
| WO | WO 94/12180 A1 | 6/1994 |
| WO | WO 97/41878 A1 | 11/1997 |
| WO | WO 97/47287 A1 | 12/1997 |
| WO | WO 88/08704 A2 | 11/1998 |
| WO | WO 99/04763 A1 | 2/1999 |
| WO | WO 00/25752 A1 | 5/2000 |
| WO | WO 00/33821 A1 | 6/2000 |
| WO | WO 00/42998 A1 | 7/2000 |

(56) References Cited

FOREIGN PATENT DOCUMENTS

| | | |
|---|---|---|
| WO | WO 00/51568 A1 | 9/2000 |
| WO | WO 00/59486 A2 | 10/2000 |
| WO | WO 01/13898 A2 | 3/2001 |
| WO | WO 01/72285 A1 | 10/2001 |
| WO | 01/80829 | 11/2001 |
| WO | WO 02/13794 A1 | 2/2002 |
| WO | WO 02/43704 A1 | 6/2002 |
| WO | WO 02/057473 A1 | 7/2002 |
| WO | WO 02/085336 A1 | 10/2002 |
| WO | WO 03/013492 A1 | 2/2003 |
| WO | WO 03/039520 A1 | 3/2003 |
| WO | WO 03/026613 A1 | 4/2003 |
| WO | 03/041683 | 5/2003 |
| WO | WO 03/043661 A1 | 5/2003 |
| WO | 03/047552 | 6/2003 |
| WO | 2004/009058 | 1/2004 |
| WO | 2004/022037 | 3/2004 |
| WO | 2004/087111 | 10/2004 |
| WO | WO 2005/097064 | 10/2005 |
| WO | WO 2005/105049 A2 | 11/2005 |

OTHER PUBLICATIONS

Bodmeier, R., et al., "Theophylline Tablets Coated with Aqueous Latexes Containing Dispersed Pore Formers," Journal of Pharmaceutical Sciences, vol. 79, No. 10, pp. 925-928 (Oct. 1990).
Copending U.S. Appl. No. 10/356,641, filed Jun. 20, 2003, Specification and currently pending claims.
Gordon et al., J. Pharmaceutical Sciences (1993), 82(2), 220-26.
"Low Substituted Hydroxyprolcellulose," Offical Monographs for Part II, 2001, NRF, JP XIV, pp. 942-943.
Ahmed, "Interview Summary," 2 pages, from U.S. Appl. No. 10/356,641 (dated Jul. 29, 2008).
Ahmed, "Interview Summary," 2 pages, from U.S. Appl. No. 10/356,641 (dated May 15, 2009).
Ahmed, "Interview Summary," 3 pages, from U.S. Appl. No. 10/356,641 (dated Sep. 8, 2006).
Ahmed, "Interview Summary," 4 pages, from U.S. Appl. No. 10/356,641 (dated Aug. 2, 2006).
Ahmed, "Office Action Summary," 10 pages, from U.S. Appl. No. 10/356,641 (dated Jan. 10, 2006).
Ahmed, "Office Action Summary," 13 pages, from U.S. Appl. No. 10/356,641 (dated Apr. 14, 2008).
Ahmed, "Office Action Summary," 15 pages, from U.S. Appl. No. 10/356,641 (dated Jun. 15, 2007).
Ahmed, "Office Action Summary," 20 pages, from U.S. Appl. No. 10/356,641 (dated Aug. 19, 2009).
Ahmed, "Office Action Summary," 24 pages, from U.S. Appl. No. 10/356,641 (dated Jun. 10, 2010).
Ahmed, "Office Action Summary," 44 pages, from U.S. Appl. No. 10/356,641 (dated Dec. 11, 2008).
Ahmed, "Office Action Summary," 7 pages, from U.S. Appl. No. 10/356,641 (dated Jun. 13, 2006).
Ahmed, "Office Action Summary," 7 pages, from U.S. Appl. No. 10/356,641 (dated Nov. 30, 2006).
Bauer et al., Pharmarzeutische Technologie, 5th Edition, 1997, Govi Verlag Frankfurt, pp. 164-166.
Berigan, "Atomoxetine Used Adjunctively With Selective Serotonin Reuptake Inhibitors to Treat Depression," Prim. Care. Companion J. Clin. Psychiatry 6(2):93-94 (2004).
Citation in the Third Party Observation in the Opposition of European Patent No. EP 0914818 B1.
Database WPI, Selection Ch, Week 198748, Derwent Publications, Ltd., London, GB; Class A96; AN 1987-338131, XP002156870.
Duncan, "Examination Report," 2 pages, from New Zealand Patent Appl. No. 554346, New Zeland Patent Office, Wellington, New Zealand (dated May 20, 2009).
Experimental data provided by Opponent 1 the Opposition of European Patent No. EP 0914818 B1.

Fell, Letter to The Editor, J. Pharm. Pharmocal. 1968, vol. 20, pp. 657-658.
FMC Corporation Product Specification for Avicel PH, 2005.
Foreign non-patent publication from Japanese textbook, 1989, Hirokawa Publishing Co.
Foreign non-patent publication Sysmex No. PP30SCJ001.
Gorman et al., An Evaluation of Croscarmellose as a Tablet Disintegrant in Direct Compression Systems, Drug, Dev. Ind. Pharm. 1982; vol. 8, pp. 397-410.
Handbook (Binran) of Granule, vol. 1, Ohmsho Ltd., pp. 434 & 438 (May 3, 1975).
Kaneto et al., 2000, Latest Pharmacy, Hirokawa Publishing Co., I Edition, (Extract and English translation thereof).
Kawashima, "Low-Substituted Hydroxyproylcellulose as a Sustained-Drug Release Matrix Base or Disintegrant Depending on Its Particle Size and Loading in Formulation," Pharm. Res. 1993, vol. 10(3), pp. 351-355.
Kornblum, "A New Tablet Disintegrating Agent," J. Pharm. Sci., Jan. 1973, vol. 62(1), pp. 43-49.
Kratochvil et al., "Atomoxetine: a selective noradrenaline reuptake inhibitor for the treatment of attention-deficit/hyperactivity disorder," Expert Opin. Pharmacother, 4(7):1165-1174 (2003).
McKenna et al., "Effect of particle size on the compaction mechanism and tensile strength of tablets," J. Pharm. Pharmacol, Jun. 1982, vol. 34(6), pp. 347-351.
McKetta et al., "Table of Contents," Encyclopedia of Chemical Processing and Design (1989).
McKetta et al., Encyclopedia of Chemical Processing and Design., "Organic Phase Separation Conservation," p. 167 (1989).
Mitsuo et al., Pharmaceutics Manual, 1989, Pharmaceutics Manual, Nanzando Co. Ltd. (Extract and English translation thereof).
Observations issued by the European Patent Office dated Aug. 16, 2002 regarding European Application No. 0914818 (Applicant Kyowa Hakko Kogyo Co., Ltd.)
Oh, "International Preliminary Report on Patentability," 5 pages, from International Appl. No. PCT/US2005/037084, United States Patent and Trademark Office, Alexandria, Virginia, USA (dated Aug. 24, 2007).
Opposition Documents related to European Opposition of EP 0914818B1 (Opposition file history as of Mar. 9, 2009, excluding duplicative, purely administrative documents (97 pages total), as indicated in the accompanying Information Disclosure Statement submitted herewith).
Packard, "Advisory Action Before the Filing of an Appeal Brief," 5 pages from U.S. Appl. No. 11/223,819 (dated Jun. 24, 2010).
Packard, "Office Action Summary," 16 pages from U.S. Appl. No. 11/223,819 (dated Feb. 24, 2009.)
Packard, "Office Action Summary," 8 pages from U.S. Appl. No. 11/223,819 (dated Aug. 22, 2008).
Packard, "Office Action Summary," 9 pages from U.S. Appl. No. 11/223,819 (dated Dec. 7, 2009).
Pharmaceutical Excipients. London: Pharmaceutical Press, Electronic Version, 2006, Mannitol.
Pharmaceutical Excipients. London: Pharmaceutical Press. Electronic Version, 2006, Lactose Monohydrate.
Pharmaceutical Excipients. London: Pharmaceutical Press. Electronic Version, 2006, Croscarmellose sodium.
Rudnic et al., "Some Effects of Relatively Low Levels of Eight Tablet Disintegrants on a Direct Compression System," Drug. Dev. Ind. Pharm., 1981, vol. 7(3), pp. 347-358.
Rundic et al., "Studies of the Utility of Cross Linked Polyvinlpolypreolidine as a Tablet Disintegrant," Drug Development and Industrial Pharmacy, 1980, vol. 6, No. 3, pp. 291-309.
Sato et al., "Anticonvulsant effects of tigabine, a new antiepileptic drug: the profile of action in the rat kindling model of epilepsy," Epilepsia 37 (Supp.3): 110-111 (1996).
Schifferer, "Communication pursuant to Article 94(3) EPC," 3 pages, from European Patent Appl. No. 05851221.1, European Patent Office, Munich, Germany (dated Oct. 13, 2009).
Schifferer, "International Search Report," 4 pages, from International Appl. No. PCT/US2005/037084, European Patent Office, Rijswijk, The Netherlands (dated Jun. 1, 2006).

(56) References Cited

OTHER PUBLICATIONS

Schifferer, "Written Opinion of the International Search Authority," 6 pages, from International Appl. No. PCT/US2005/037084, European Patent Office, Munich, Germany (dated Jun. 1, 2006).
Shangraw et al., "A new era of tablet disintegrants," Pharm. Technol. 1980, vol. 4(10), pp. 49-57.
Spear, "Office Action Summary," 16 pages, from U.S. Appl. No. 10/356,641 (dated Dec. 8, 2004).
Trouier and Wood, 2005, "Particle Size Measurement," Kirk-Orhmer Encoclopedia of Chemical Technology (Extract of 1. Introduction; 2. Data Representation; 4. Measurement Metholds: 8 Selection of Equipment).
Van Kamp et al., "Improvement by super disintegrants of the properties of tablets containing lactose, prepared by wet granulation," Pharmaceutisch Weekblad Scientific Edition; 1983, vol. 5, pp. 165-171.
Villa, "Communication pursuant to Article 94(3) EPC," 3 pages, from European Patent Appl. No. 05818156.1, European Patient Office, Munich, Germany (dated Jul. 1, 2009).
Villa, "International Search Report," 4 pages, from International Appl. No. PCT/US2005/038328, European Patent Office, Rijswijk, The Netherlands (dated Sep. 15, 2006).
Villa, "Written Opinion of the International Search Authority," 5 pages, from International Appl. No. PCT/US2005/038328, European Patent Office, Munich, Germany (dated Sep. 15, 2006).
Vromans et al., "Studies on tableting properties of lactose," Pharmaceutisch Weekblad Scientific Edition; 1985, vol. 7, pp. 186-193.
Walsh, "Examination Report," 2 pages, from New Zealand Patent Appl. No. 554240, New Zealand Patent Office, Wellington, New Zealand (dated Jun. 9, 2009).
Ware, "Office Action Summary," 12 pages, from U.S. Appl. No. 09/147,374 (dated Oct. 14, 1999).
Ware, "Office Action Summary," 6 pages, from U.S. Appl. No. 09/147,374 (dated Jun. 30, 2000).
Ware, "Office Action Summary," 6 pages, from U.S. Appl. No. 09/147,374 (dated Aug. 29, 2001).
Ware, "Office Action Summary," 6 pages, from U.S. Appl. No. 09/147,374 (dated Jun. 4, 2002).
Ware, "Office Action Summary," 8 pages, from U.S. Appl. No. 09/147,374 (dated Apr. 18, 2001).
Welter, "Advisory Action Before the Filing of an Appeal Brief," 9 pages from U.S. Appl. No. 11/256,653 (dated Sep. 27, 2010).
Welter, "Office Action Summary," 25 pages from U.S. Appl. No. 11/256,653 (dated Mar. 18, 2010).
Welter, "Office Action Summary," 26 pages from U.S. Appl. No. 11/213,266 (dated Nov. 13, 2009).
Welter, "Office Action Summary," 28 pages from U.S. Appl. No. 11/213,266 (dated Apr. 6, 2009).
Welter, "Office Action Summary," 29 pages from U.S. Appl. No. 11/256,653 (dated Jul. 10, 2008).
Welter, "Office Action Summary," 29 pages from U.S. Appl. No. 11/256,653 (dated May 12, 2009.)
Welter, "Office Action Summary," 29 pages from U.S. Appl. No. 11/213,266 (dated Jul. 10, 2008.)
Welter, "Office Action Summary," 33 pages from U.S. Appl. No. 11/213,266 (dated Nov. 12, 2010).
Chandra, "Examiner's first report on paten application 2005299490," 2 pages, Australia patent application No. 2005299490 (dated Mar. 12, 2010).
Villa, "Communication pursuant to Article 94(3) EPC," 4 pages, from European Patent Appl. No. 05818156.1, European Patent Office (dated Feb. 25, 2011).
Walsh, "Examination Report," 2 pages, from New Zealand Patent Appl. No. 589750, New Zealand Patent Office (dated Dec. 8, 2010).
Office Action, Mexico patent application No. MX/a/2007/004741, 3 pages, Mexico Patent Office (dated Oct. 12, 2010).
Welter, Office Action, 24 pages, U.S. Appl. No. 12/466,855, United States Patent and Trademark Office (dated Mar. 17, 2011).
Potenza, Examiner's first report on patent application No. 2005307052, 3 pages, Australia Patent Office (dated Mar. 15, 2010).
Schifferer, "Communication," 9 pages, from European Pat. Appl. No. 10184903.2, European Patent Office (dated Mar. 17, 2011).
Albrecht, "International Search Report," 6 pages, from International Patent Appl. No. PCT/US02/31535, European Patent Office (dated Feb. 3, 2003).
Anwar et al., "Chronotherapeutics for Cardiovascular Disease," Drugs 55(5):631-643 (1998).
Fubara, "International Preliminary Examination Report," 3 pages, from International Patent Appl. No. PCT/US02/31535, European Patent Office (dated Jun. 19, 2003).
Ishino et al., "Design and Preparation of Pulsatile Release Tablet as a New Oral Drug Delivery System," Chem. Pharm. Bull. 40(11):3036-3041 (1992).
Nwokole et al., "Tolerance during 29 days of conventional dosing with cimetidine, mizatidine, famotidine or ranitidine," Aliment. Pharmacol. Ther. 4(Suppl. 1):29-45 (1990) Abstract only.
Ohira et al., "Effects of Various Histamine $H_2$-Receptor Antagonists on Gastrointestinal Motility and Gastric Emptying," J. Smooth Muscle Res. 29:131-142 (1993).
Rankin, "International Search Report," 6 pages, PCT International Application No. PCT/US02/39238, European Patent Office (dated May 8, 2003).
Ueki et al., "Nizatidine Comparably Enhances Postprandial Gastric Motility to Existing Gastroprokinetics in Dogs," Jpn. Pharmacol. Ther. 28(11):925-930 (2000).
Uhl, "International Search Report," 5 pages, International Patent Appl. No. PCT/US2006/016538, European Patent Office (dated Feb. 27, 2007).
Uhl, "Written Opinion of the International Searching Authority," 6 pages, International Patent Appl. No. PCT/US2006/016538, European Patent Office (dated Feb. 27, 2007).
Villa, "European Search Report," 5 pages, from European Patent Appl. No. 11171982.9, European Patent Office, Munich, Germany (dated Dec. 22, 2011).
Yamahara et al., "Effect of release rate on bioavailability of control-release multiple unit dosage forms," Yakuzaigaku 55(2):99-107 (1995).
Yamamoto et al., "The Effects of Nizatidine on the Function of Esophageal Motility in Patients with Gastroesophageal Reflux Disease (GERD)," Jpn. Pharmacol. Ther. 28(5):419-424 (2000).
Young, "International Preliminary Examination Report" 6 pages, PCT International Application No. PCT/US02/39238, United States Patent and Trademark Office (dated Apr. 27, 2005).
Young, "International Search Report," 2 pages, PCT appl. No. PCT/US11/20493, United States Patent and Trademark Office (dated Mar. 23, 2011).
Young, "Written Opinion of the International Searching Authority," 6 pages, PCT appl. No. PCT/US11/20493, United States Patent and Trademark Office (dated Mar. 23, 2011).
Young, "Written Opinion," 5 pages, PCT International Application No. PCT/US02/39238, United States Patent and Trademark Office (dated Jan. 13, 2005).
Zheng et al., "Influence of Eudragit® NE 30 D Blended with Eudragit® L 30 D-55 on the Release of Phenylpropanolamine Hydrochloride from Coated Pellets," Drug Development and Industrial Pharmacy 29(3):357-366 (2003).
Zimmer, "European Search Report," 3 pages, European patent appl. No. 01103129.1, European Patent Office (dated Jun. 9, 2001).
Zimmer, "International Search Report," 4 pages, PCT International Application No. PCT/US01/04012, European Patent Office (dated Jun. 19, 2001).

* cited by examiner

TASTE-MASKED PHARMACEUTICAL COMPOSITIONS

CROSS REFERENCE TO RELATED APPLICATION

This application claims the benefit of U.S. Provisional Application No. 60/617,737, filed Oct. 12, 2004, which is hereby incorporated by reference.

TECHNICAL FIELD

This invention relates to an orally disintegrating tablet (ODT) composition comprising taste-masked microparticles of one or more active pharmaceutical ingredients suitable for oral administration for the treatment of diseases and rapidly-dispersing microgranules comprising a disintegrant and a sugar alcohol or a saccharide, or a mixture thereof, each of which have an average particle diameter of not more than about 30 μm. The multi-particulate ODT composition comprising rapidly-dispersing microgranules and drug-containing core particles (crystals or granules, beads or pellets of one or more active pharmaceutical ingredients) coated with a taste-masking membrane comprising a blend of a water-insoluble polymer with a gastrosoluble polymer, rapidly disintegrates on contact with saliva when placed in the oral cavity forming a smooth, easy-to-swallow suspension containing coated drug particles exhibiting acceptable taste-masking and provides rapid, substantially-complete release of the dose on entry into the stomach, thereby enhancing the probability of achieving bioequivalence to the reference immediate release (IR) product. The invention additionally provides a method of manufacturing orally disintegrating tablets comprising rapidly-dispersing microgranules and acceptably taste-masked microparticles, each population having an average particle size of not more than about 400 μm, preferably not more than about 300 μm, to provide a smooth mouthfeel leaving no aftertaste (non-gritty or non-chalky taste) after swallowing the suspension.

BACKGROUND OF THE INVENTION

There are two types of most widely used dosage forms for oral administration: tablets and capsules. However, such dosage forms have several disadvantages. For example, it is estimated that 50% of the population have problems swallowing tablets (see Seager in Journal of Pharmacol. and Pharm. 50, pages 375-382, 1998); especially it is hard for aged persons to swallow tablets or capsules or to medicate children who are unable or unwilling to swallow tablets or capsules. This leads to poor compliance, even non-compliance, with the treatment and thus has a negative impact on the efficacy of the treatment. Many therapeutic agents are bitter. The bitter taste precludes the medication from being easily sprinkled onto food such as applesauce, a commonly used method of administering medications to children. The conventional capsule or tablet dosage form is also inconvenient for the "people on the move" who often do not have access to drinking water or fluids. Chewable tablets comprising taste-masked particles capable of being chewed without experiencing a bitter taste were introduced not too long ago, and these tablets became popular with children.

The bitter drug-containing cores incorporated into chewable tablets have thick coatings of mostly water-insoluble polymers such as ethylcellulose to resist fracture during tablet compression and/or during chewing and concomitant leakage of the bitter active. Consequently, substantially complete release of the drug from such chewable tablets in the gastrointestinal tract may take 2 hours or longer. More recently, orally disintegrating tablet (ODT) dosage forms have been introduced, which rapidly dissolve or disintegrate in the buccal cavity and hence can be taken without water. Such medicines are convenient for all, aged persons, children or "people on the move".

An ideal orally disintegrating tablet formulation comprising rapidly-dispersing granules and drug-particles (crystals, pellets, granules, or beads containing the drug) with a taste-masking membrane (if required) should rapidly disintegrate on contact with saliva in the oral cavity forming a smooth, easy-to-swallow suspension containing taste-masked drug particles having an average particle diameter of not more than about 400 μm to provide a smooth mouthfeel leaving no aftertaste (i.e., little or minimal drug release with a non-gritty or non-chalky taste) until swallowed, and should provide rapid, substantially-complete release upon arrival in the stomach in order to be bioequivalent to the immediate-release reference-listed-drug product.

As indicated earlier, most of the actives in the marketed products are bitter to a varying degree. Typically, to eliminate/minimize drug-release in the oral cavity, the bitter drug substance was taste-masked in the prior art by providing a thick polymer-membrane around the drug particle typically by microencapsulation (coacervation by phase separation) or fluid-bed coating for preparing immediate release dosage forms (chewable tablets, sprinkles, sachets, suspensions). However, coating with water-insoluble polymers such as ethylcellulose (EC), cellulose acetate (CA), cellulose acetate phthalate, polyvinyl acetate, Eudragit® RS, RL, L, S and NE30D polymers, results in slower dissolution profiles and not-too-infrequently results in imparting sustained-release properties.

Several marketed products, which are typically conventional or effervescent based immediate-release dosage forms, have a $T_{max}$ of less than an hour and rapid-onset of action. An undesirable consequence of taste-masking in general is the slower release of the drug in the gastrointestinal tract. Eudragit® E (EPO or E100), a copolymer consisting of dimethylaminoethyl methacrylate and neutral methacrylic acid esters with a weight-average molecular weight of 150,000 and a $pK_a$ of 6.3, is readily soluble under acidic conditions after protonation of the substituted amino groups. In a neutral or alkaline environment, the polymer swells and the coating film becomes water-permeable and the polymer film slowly erodes and dissolves. The saliva is typically in the pH range of 6.7 to 7.4. Hence, it is likely that one achieves effective taste-masking in the oral cavity for a limited time if the drug core is coated with Eudragit E100/EPO alone or in combination with a water-soluble agent.

From a pharmaceutical and a practical point of view, the inventors of the present invention have examined various methods of taste-masking bitter active pharmaceutical ingredients suitable for incorporation into orally disintegrating tablets having the property of rapidly disintegrating in the buccal cavity and leaving no aftertaste (good creamy mouthfeel) and additionally providing rapid, substantially-complete release of the dose in the stomach, thereby enhancing the probability of achieving bioequivalence to the reference product with a rapid-onset of action. The method of producing taste-masked microparticles (mean particle size of about 100-400 μm) in accordance with the present invention comprising one or more bitter active pharmaceutical ingredient(s) includes membrane-coating of drug-containing core particles (crystals, microgranules, drug-layered or extruded/spheronized-beads) with a mixture of a water-insoluble polymer, such as ethylcellulose or polyvinyl acetate, and a gastrosoluble polymer, such as Eudragit E100, at a ratio of about 50/50 to 95/5 for a weight gain of not less than about 5% and not more than about 50% by weight, based on total weight of the coated particle. Furthermore, the microparticles prepared in accordance with the present invention can be produced to exhibit the specified criteria (viz., desired particle size distribution, little or minimal release of the bitter active in the mouth (hence no aftertaste), and rapid-release of the dose from the taste-masked microparticles upon entry into the stomach) to be suitable for incorporation into orally disintegrating tablets. In accordance with particular embodiments, both the water-insoluble polymer and the gastrosoluble polymer are dissolved in the same solvent system and sprayed on to drug-containing particles in a fluid-bed coater. Hence, one can expect to find, without going into the mechanism, a random but homogeneous disposition of individual polymer molecules in the membrane. As the gastric fluid rapidly penetrates into the bead-core, one can expect to find microchannels being formed ensuring rapid release of the active.

The taste-masking effectiveness is measured by the percent of the dose released in a simulated saliva fluid at a pH of 6.7-7.4. The smaller the percent release, the more effective the taste-masking. A pharmaceutical composition with a release of not more than 10% of the dose in about 3 minutes in a simulated saliva fluid (the longest anticipated residence time for taste-masked microparticles in the mouth) is considered acceptably taste-masked. On the other hand, the drug release on oral administration is evaluated by measuring the percent of the dose released in an acidic pH of about 1.2. The faster the release of the drug from the taste-masked microparticles in the stomach, the higher the probability of being bioequivalent to the reference product. A release of not less than about 60% of the dose in about 30 minutes in the acidic buffer is considered acceptable for achieving bioequivalence to the reference product.

SUMMARY OF THE INVENTION

The present invention provides pharmaceutical compositions and methods for making taste-masked microparticles and orally disintegrating tablets. In accordance with particular embodiments, the compositions may provide effective taste-masking, smooth mouthfeel (no aftertaste) and rapid/complete release upon reaching the stomach, thereby enhancing the probability of achieving bioequivalence to the reference product.

The multi-particulate compositions comprise taste-masked core particles (crystals or granules, beads or pellets comprising one or more bitter-tasting active pharmaceutical ingredients) produced by coating with a mixture of a water-insoluble polymer and a gastrosoluble polymer. The taste-masked composition prepared in accordance with the present invention rapidly releases the drug, i.e., not less than about 60% of the dose released in 30 minutes when tested for dissolution using United States Pharmacopoeia Apparatus 1 (baskets @ 100 rpm) or 2 (paddles @ 50 rpm) in 900 mL of 0.1N HCl. Another embodiment of the invention relates to a pharmaceutical composition in the form of an orally disintegrating tablet comprising (i) rapidly-dispersing microgranules comprising (a) a disintegrant and (b) a sugar alcohol or a saccharide whose average particle size is not more than about 30 μm, (ii) microparticles of one or more bitter-tasting active pharmaceutical ingredients taste-masked with a polymer membrane comprising a blend of a water-insoluble polymer and a gastrosoluble polymer and (iii) optionally other pharmaceutically acceptable excipients. In accordance with particular embodiments, these orally disintegrating tablets have the properties of disintegrating on contact with saliva in the buccal cavity in about 60 seconds forming a smooth easy-to-swallow suspension with no aftertaste (good creamy mouthfeel) and rapidly releasing the dose on entry into the stomach, thus enhancing the probability of being bioequivalent to the reference product.

In accordance with one aspect of the invention, a taste-masked multiparticulate pharmaceutical composition comprising:
(a) a drug-containing core particle (crystal, granule, pellet, bead and the like);
(b) a taste-masking membrane on said drug-containing core particle comprising a combination of a water-insoluble polymer and a gastrosoluble polymer at a ratio ranging from about 95/5 to about 50/50 having a thickness of from about 5% to about 50% based on the weight of the coated particle and an average particle size of not more than about 400 μm is disclosed.

In accordance with certain embodiments, the composition exhibits acceptable taste-masking when the composition is placed in the oral cavity for 3 minutes, preferably for 2 minutes and more preferably for 60 seconds, most preferably until it is swallowed leaving little or no aftertaste (i.e., experiencing no gritty or chalky taste) and the composition provides rapid, substantially-complete release of the dose upon entry into the stomach, i.e., releases not less than 60% of the dose in 30 min when tested for dissolution using United States Pharmacopoeia Apparatus 1 (Baskets@ 100 rpm in 900 mL of pH 1.2 buffer).

A taste-masked multiparticulate pharmaceutical composition in the ODT (orally disintegrating tablet) form, which disintegrates on contact with saliva in the buccal cavity in about 60 seconds forming a smooth easy-to-swallow suspension (no gritty or chalky aftertaste) is also disclosed. The ODT may comprise the drug-containing core particle (crystal, granule, pellet, bead and the like), with a taste-masking membrane on the drug-containing core particle. The taste-masking membrane may comprise a water-insoluble polymer and a gastrosoluble polymer at a ratio ranging from about 95/5 to about 50/50 having a thickness of from about 5% to about 50% based on the weight of the coated microparticle with an average particle size of not more than about 400 μm, or in some embodiments not more than 300 μm. The ODT may also include a rapidly-dispersing microgranule with an average particle size of not more than about 300 μm, or in some embodiments not more than 200 μm, comprising a disintegrant and a sugar alcohol or a saccharide or a combination thereof, each having an average particle diameter of not more than about 30 μm, and optionally pharmaceutically acceptable excipients typically used in ODT formulations, viz., flavors, a sweetener, coloring agents, and a disintegrant.

The ODT in accordance with one embodiment exhibits the following properties:
1) disintegrates on contact with saliva in the oral cavity in about 60 seconds forming a smooth, easy-to-swallow suspension comprising taste-masked microparticles and
2) taste-masked microparticles provide rapid, substantially-complete release of the dose upon entry into the stomach.

The ODT may comprise taste-masked microparticles demonstrating effective taste-masking by releasing not more than 10% in about 3 minutes (the longest typical residence time anticipated for the ODT in the buccal cavity) when dissolution tested in a simulated saliva fluid (pH 6.8) while releasing not less than 60% of the dose in about 30 minutes when dissolution tested in 0.1N HCl.

A method of manufacturing a taste-masked multi-particulate composition wherein the dosage form comprises one or more active pharmaceutical ingredient(s) in sufficient quantities to be administered orally to a patient at prescribed dosing regimen to provide therapeutic efficacy is also provided.

The taste-masked multiparticulate pharmaceutical composition may include any pharmaceutically acceptable active ingredient requiring taste-masking.

In accordance with particular embodiments, the method of preparing a taste-masked multi-particulate composition includes layering a pharmaceutically acceptable drug from a polymeric binder solution onto an inert particle selected from the group consisting of sugar spheres and cellulose spheres. Fluid bed or pan coating may be used to apply the active and polymeric binder solution.

In accordance with certain embodiments, the drug-containing particle is a microgranule or an extruded/spheronized pellet comprising one or more pharmaceutically acceptable active ingredient(s), a polymeric binder, which imparts resilient characteristics to dried microgranules, a hydrophilic filler/diluent, and optionally a flavor, a sweetener and/or a disintegrant.

The microgranules of one or more active pharmaceutical ingredient(s) may be prepared by a conventional high-shear or planetary granulation process or the pellets may be prepared by a conventional granulation-extrusion-spheronization process comprising an active pharmaceutical ingredient, a polymer binder and one or more fillers/diluents.

The water-insoluble polymer (preferably ethylcellulose with an average viscosity of 10 cps) and the gastrosoluble polymer (preferably Eudragit EPO) may be present at a weight ratio of from about 95/5 to 50/50, more particularly from about 85/15 to 65/35, and the membrane thickness varying from about 5% to 50%, more particularly from about 10% to 30%, by weight in accordance with particular embodiments.

In accordance with some particularly useful embodiments, the taste-masked multiparticulate pharmaceutical composition includes rapidly-dispersing microgranules comprising a disintegrant, preferably crospovidone, and a sugar alcohol (preferred mannitol) or a saccharide (lactose) or a combination thereof, each having an average particle diameter of not more than about 30 μm and a ratio of sugar alcohol and/or saccharide to disintegrant varying from about 90/10 to about 99/1.

The rapidly-dispersing microgranules and taste-masked microparticles may be present in the ratio of about 6/1 to 2/1, more particularly from about 4/1 to 3/1, to achieve a smooth mouthfeel in some embodiments of the taste-masked composition.

A method of manufacturing a taste-masked multi-particulate composition of one or more active pharmaceutical ingredient(s) is also provided. The method may comprise the steps of:
  a) preparing core particles of one or more active pharmaceutical ingredient(s) as granules by a conventional granulation process, as beads by drug-layering onto inert particles from a polymeric binder solution in a fluid-bed equipment, or as microgranules or as pellets by a conventional granulation of one or more active pharmaceutical ingredient(s), one or more polymeric binder(s), a hydrophilic filler/diluent, and optionally a flavor, a sweetener, and/or a disintegrant or granulation-extrusion-spheronization process; and
  b) coating core particles by applying a membrane comprising a mixture (at a ratio of 95/5 to 50/50) of water-insoluble ethylcellulose and gastrosoluble Eudragit E100 dissolved in a mixture of acetone and purified water, the membrane coating comprising approximately from about 5% to about 50% based on the total weight of the coated particles.

The composition may exhibit the following properties:
1) acceptable taste-masking when the composition is placed in the oral cavity for 3 minutes, more particularly for 2 minutes and in certain embodiments for 60 seconds, and in still other embodiments, until it is swallowed leaving no aftertaste; and
2) rapid substantially complete release of the dose upon entry into the stomach, i.e., releases not less than 60% of the dose in 30 min when tested for dissolution using United States Pharmacopoeia Apparatus 1 (Baskets @ 100 rpm) or Apparatus 2 (paddles @ 50 rpm in 900 mL of pH 1.2 buffer).

In a particular embodiment of the invention, the method comprises the steps of:
  a) preparing core particles (crystals with a particle size distribution of 20-500 μm, more particularly from about 50-300 μm, beads, microgranules, pellets) of one or more active pharmaceutical ingredient(s) as described above;
  b) taste-masking core particles by applying a membrane comprising a mixture of water-insoluble and gastrosoluble polymers as described above, the membrane coating comprising approximately from about 5% to about 50% based on the total weight of the coated particles;
  c) granulating a disintegrant such as crospovidone with a sugar alcohol or a saccharide, or a combination thereof, each having an average particle diameter of not more than 30 μm, with water or an alcohol-water mixture in a conventional granulator and drying in a fluid bed equipment to produce granules with an average particle size not more than 400 μm (more particularly not more than 300 μm);
  d) blending taste-masked microparticles of step (b) with rapidly disintegrating microgranules of step (c) and other optionally acceptable ingredients such as a flavoring agent, a coloring agent, a sweetener and additional disintegrant in sufficient quantities; and
  e) compressing into tablets using a conventional rotary tablet press equipped with an external lubrication system to pre-lubricate the dies and punches The ODT may exhibit the following properties:
1) disintegrates on contact with the saliva in the oral cavity forming a smooth, easy-to-swallow suspension comprising taste-masked microparticles,
2) leaves no aftertaste after swallowed (no gritty or chalky mouthfeel),
3) provides rapid, substantially-complete release of the dose upon entry into the stomach; or
4) the ODT when tested for dissolution using United States Pharmacopoeia Apparatus 1 (baskets @ 100 rpm) or Apparatus 2 (paddles @ 50 rpm) in 900 mL buffer releases not more than 10% of the dose in about 3 minutes in a simulated saliva buffer at pH 6.8 and not less than 60% of the dose in about 30 minutes in an acidic buffer at pH 1.2.

These and other embodiments, advantages and features of the present invention become clear when detailed description and examples are provided in subsequent sections.

DETAILED DESCRIPTION OF THE INVENTION

Figure 1:
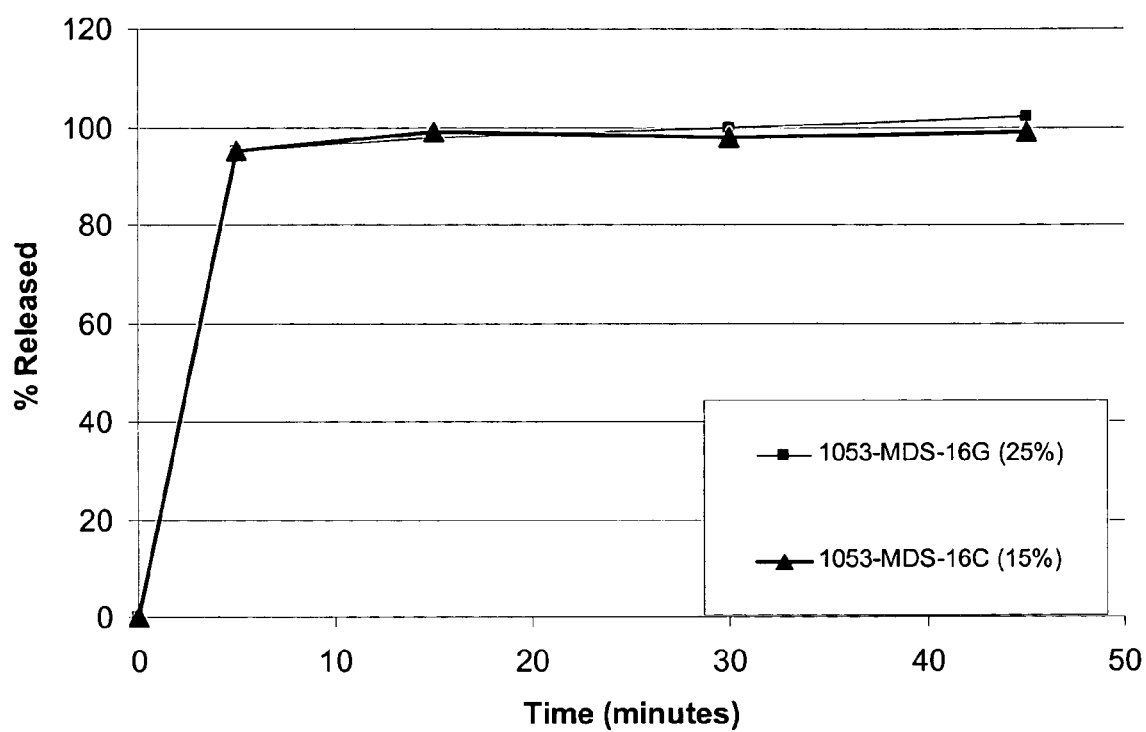
FIG. 1 illustrates the dissolution profiles in 0.1N HCl of taste-masked diphenhydramine citrate beads of Example 1.

All documents cited are, in relevant part, incorporated herein by reference; the citation of any document is not to be construed as an admission that it is prior art with respect to the present invention.

The term "drug", "active" or "active pharmaceutical ingredient" as used herein is meant to include the base, any pharmaceutically acceptable salt, stereo-isomer and a mixture thereof. The term represents any therapeutic agent indicated for oral administration. Examples include, but are not limited to, NSAID analgesic, histamine $H_1$-receptor antagonist, histamine $H_2$-receptor antagonist, 5-$HT_1$ receptor agonist, 5-$HT_3$ receptor antagonist, antiepileptic drug, centrally acting adrenergic agonist, sleep-aid, leukotriene receptor antagonist, or drug for the treatment of erectile dysfunction, requiring taste-masking. Specific examples of the therapeutic agent used in various embodiments of this invention include one or more agents selected from the group consisting of sumatriptan, electriptan, cetirizine, zafirlukast, montelukast, famotidine, ranitidine, tiagabine, fexofenadine, tizanidine, ondansetron, granisetron, zolpidem, zaleplon, sildenafil, tadalafil, and the like.

An aqueous or a pharmaceutically acceptable solvent medium may be used for preparing drug containing core particles for taste-masking, viz., beads by drug-layering onto inert sugar spheres in fluid-bed equipment. Examples of useful solvents include, but are not limited to acetone, ethanol, isopropanol, water or mixtures thereof. The type of film forming binder that is used to bind the water-soluble drug to the inert sugar sphere is not critical but usually water-soluble, alcohol-soluble or acetone/water soluble binders are used. A binder such as polyvinylpyrrolidone (PVP), polyethylene oxide, hydroxypropyl methylcellulose (HPMC), hydroxypropylcellulose (HPC), may be used at concentrations of about 0.5 to 10 weight % based on the drug-layered beads. The drug substance may be present in this coating formulation in solution form or may be suspended at a solid content up to about 35% depending on the viscosity of the coating formulation.

Crystals of a bitter API with a desired particle size range (typically from about 20 μm to 500 μm, more particularly from about 50 μm to 300 μm) can be taste-masked directly. Alternatively, microgranules containing milled or micronized drug particles can be produced by granulating in a high-shear granulator the active and a suitable filler/diluent (if required) with a polymeric binder, which imparts resilient characteristics to the dried microgranules to resist attrition due to fluidization during fluid-bed coating for taste-masking. The relative amounts of active, binder and optional filler/diluent may vary considerably depending on the particular active and the dosage form. Typically, microgranules prepared in accordance with this aspect of the invention will contain from about 5% to about 95%, more particularly from about 20% to about 90%, active and up to about 15% binder with any optional filler/diluent being present at from about 0% to 90%, more particularly from about 20% to 80%, by weight of the microgranules.

Useful polymeric binders include, without limitation, hydroxypropylcellulose (Klucel® LF from Aqualon), modified starch (e.g., Starch 1551 and Starch 1500, commercially available from National Starch and Colorcon, respectively), Kollidon® VA 64, poly(vinyl acetate-vinylpyrrolidone) from BASF, and hydroxypropyl methylcellulose with a viscosity of 100 cps or more (e.g., Methocel K100LV and Metolose K400 commercially available from Dow Chemical and Shin Etsu Chemicals, respectively) alone or in combination with a widely used binder such as PVP (polyvinylpyrrolidone) and hydroxypropyl methylcellulose with a viscosity of 15 cps or less.

Examples of useful pharmaceutically acceptable fillers/diluents include, but are not limited to, mannitol, lactose, microcrystalline cellulose, potassium sulfate, calcium phosphate, modified starch and mixtures thereof.

The water-insoluble polymers suitable for taste-masking of bitter drugs by coating in fluid-bed equipment include, but are not limited to, ethylcellulose, cellulose acetate, cellulose acetate butyrate, methacrylate copolymers available under the trade name of Eudragit® (type RL, RS and NE30D). The gastrosoluble polymers include, but are not limited to, maltrin, an aminoalkyl methacrylate copolymer available under the trade name of Eudragit® (type E100 or EPO), polyvinylacetal diethylaminoacetate e.g., AEA® available from Sankyo Company Limited, Tokyo (Japan), and the like. The ratio of water-insoluble polymer to gastrosoluble polymer for producing taste-masked particles may typically vary from about 95/5 to about 50/50, or in some embodiments from about 85/15 to 65/35, at a thickness of from about 5% to about 50%, or in some embodiments from about 10% to about 30% by weight of the coated bead.

The membranes described herein may also include one or more plasticizers. Representative examples of plasticizers that may be used to plasticize the membranes include triacetin, tributyl citrate, triethyl citrate, acetyl tri-n-butyl citrate, polyethylene glycol, polypropylene glycol, diethyl phthalate, castor oil, dibutyl sebacate, acetylated monoglycerides and the like or mixtures thereof. The plasticizer may comprise typically about 10-30% or about 5-15% based on the weight of dry polymer, depending on the use of polymer dispersions or solutions.

The membranes described herein may also include one or more anti-tacky agents. Representative examples of anti-tacky agents that may be used include, without limitation, talc and magnesium stearate.

The ODT composition described herein typically include rapidly-dispersing microgranules. One or more sugar alcohols and/or saccharides and a disintegrant are granulated in a high-shear granulator and dried in fluid bed equipment to produce rapidly-dispersing microgranules. Rapidly-dispersing microgranules typically will contain sugar alcohol and/or saccharide and disintegrant at a ratio varying from about 90/10 to about 99/1, or in some embodiments from about 90/10 to about 95/5 by weight (sugar alcohol and/or saccharide to disintegrant). The sugar alcohol may be selected from the group consisting of mannitol, sorbitol, xylitol, maltitol and the like while the saccharide may be selected from the group consisting of lactose, sucrose, maltose or as a mixture of two or more, each of which is characterized by an average particle size of not more than about 30 μm. A disintegrant or a so-called super-disintegrant may be selected from the group consisting of crospovidone (cross-linked PVP), sodium starch glycolate, crosslinked sodium carboxymethyl cellulose, and low substituted hydroxypropylcellulose.

The ODT compositions may also include additional disintegrant separate from the rapidly dispersing microgranules. The additional disintegrant may be present in the ODT formulation at up to about 10% based on the tablet weight.

It is to be understood that while the invention has been described in conjunction with the preferred specific embodiments thereof, that the description above as well as the examples that follow are intended to illustrate and not limit the scope of the invention. Any modification within the scope of the invention will be apparent to those skilled in the art to which the invention pertains.

One method of producing taste-masked microparticles (mean particle size of about 100-400 μm) comprising one or more bitter active pharmaceutical ingredient(s) may include (i) preparing drug-containing particles (crystals with a desired particle size range (from about 20 μm to 500 μm), microgranules, drug-layered or extruded/spheronized-beads) and (ii) membrane-coating of these drug-containing particles for taste-masking. The method of producing drug-layered beads in accordance with one aspect of the invention includes dissolving or suspending one or more active pharmaceutical ingredients in a polymeric binder solution and layering onto inert particles such as sugar spheres or Celphere (50-100 mesh or 150-300 μm) using a fluid-bed coater equipped with a bottom-spray Wurster insert. Another embodiment of the method of producing resilient drug-containing microgranules, which undergo little or minimal attrition during membrane coating in fluid-bed equipment, includes granulating one or more actives and a filler or diluent (if needed) with a polymeric binder solution in a high-shear granulator. Yet another embodiment of the method of producing drug-containing beads includes granulating the active in a high-shear granulator as described above, followed by extrusion and spheronization of the wet mass using extrusion-spheronization equipment.

The method of producing taste-masked microparticles (crystals, microgranules, drug-layered or extruded/spheronized-beads) in accordance with one aspect of the invention includes fluid-bed coating with a mixture of a water-insoluble polymer such as ethylcellulose or polyvinyl acetate and a gastrosoluble polymer such as Eudragit E100 or AEA® (polyvinylacetal diethylaminoactate) at a ratio of about 50/50 to 95/5, more particularly at a ratio of about 50/50 to 80/20, and in accordance with certain embodiments at a ratio of about 50/50 to 65/35, for a weight gain of from about 5% to about 50%, preferably from about 10% to about 30%. One embodiment of the invention includes dissolving water-insoluble polymer (e.g., ethylcellulose) and gastrosoluble polymer (e.g., Eudragit EPO) in a 95/5 acetone/water with triethyl citrate (TEC) as the plasticizer (at about 10% of the weight of ethylcellulose) and with talc as the anti-tacking agent at up to about 20% by weight of the gastrosoluble polymer, and coating the drug-cores (crystals, drug-layered beads, microgranules or pellets) in a fluid-bed coater equipped with a bottom-spray Wurster insert.

The invention also provides a method of manufacturing in accordance with one aspect of the invention orally disintegrating tablets, produced by mixing taste-masked microparticles, rapidly-dispersing microgranules and optionally one or more other excipients (for example: flavor, color, sweetener etc) and compressing the blend into orally disintegrating tablets. In accordance with certain aspects of the invention, the orally disintegrating tablets rapidly disintegrate on contact with saliva in the buccal cavity leaving little or no aftertaste (good creamy mouthfeel) and provide rapid, substantially-complete release of the dose in the stomach, thereby enhancing the probability of achieving bioequivalence to the reference product.

Rapidly-dispersing microgranules may be produced in accordance with the method of manufacturing rapidly-dispersing microgranules disclosed in a co-pending U.S. patent application Ser. No. 10/827,106, filed Apr. 19, 2004 and co-pending U.S. patent application Ser. No. 11/213,266 filed Aug. 26, 2005, the contents of which are hereby incorporated by reference. Rapidly dispersing microgranules with an average particle size of about 125-300 μm, more particularly from about 150-200 μm, comprising a disintegrant (for example, Crospovidone XL-10) and a sugar alcohol or a saccharide or a mixture thereof (for example, D-mannitol) having an average particle diameter of not more than about 30 μm, may be produced by granulating with only water in a high-shear granulator, wet milling and drying in fluid bed equipment. The taste-masked microparticles produced in accordance with the present invention and rapidly-dispersible microgranules may be blended with other pharmaceutically acceptable ingredients and compressed into tablets. The tablets rapidly disintegrate (e.g., typically in less than about 60 seconds) in the buccal cavity with a smooth creamy mouth feel.

It is yet another embodiment of the invention to provide a method to manufacture rapidly disintegrating tablets, which are characterized by the property that the tablets are formed by compressing in a tablet press equipped with an external lubricating system to pre-lubricate dies and punches and the tablet formulation otherwise being free of lubricant. The orally disintegrating tablets thus produced in accordance with certain embodiments, exhibit sufficient hardness and sufficiently low friability and are suitable for packaging in HDPE bottles and push-through blister packs using conventional equipment for storage, transportation and commercial distribution.

The pharmaceutical taste-masked multi-particulate composition according to certain aspects of the present invention provides acceptable taste-masking when placed in the mouth until swallowed (target specification: not more than about 10% of the dose released in about 3 minutes when tested for dissolution in simulating saliva fluid at pH 6.8). If the composition is in the ODT (orally disintegrating tablet) form, the tablet typically disintegrates on contact with the saliva in the buccal cavity in about 60 seconds forming a smooth, easy-to swallow suspension, comprising taste-masked microparticles with acceptable aftertaste. In accordance with particular embodiments of the invention, these taste-masked microparticles provide substantially-complete release of the dose on entry into the stomach (target specification: not less than about 60%, more particularly not less than about 75% and in accordance with certain embodiments not less than about 80% of the dose released in about 30 minutes when tested for dissolution in simulated gastric fluid or 0.1N HCl at pH 1.2).

In accordance with one aspect of the invention, a method of manufacturing taste-masked microparticle composition of one or more bitter-tasting therapeutic agent(s), which exhibits acceptable taste-masking when placed in the oral cavity and provides a rapid-release of the dose on entry into the stomach, comprises the following steps:

a) preparing a drug containing core particle (crystal, bead, pellet or granule) by (i) drug-layering on an inert particle (e.g., a 50-100 mesh sugar sphere or a cellulose sphere (e.g., Celphere® CP-203 available from Asahi Kasei Chemicals Corporation) from a solution/suspension comprising a polymeric binder and the drug in fluid bed equipment and optionally coating with a seal-coat of Opadry® Clear, or (ii) granulating the drug and a filler/diluent such as lactose, mannitol or microcrystalline cellulose with a polymeric binder using a high-shear granulator, or (iii) granulating as above and followed by extrusion and spheronization; and b) coating the drug containing core particles with a solution of a functional polymer blend comprising a water insoluble polymer and a gastrosoluble polymer to produce effectively taste-masked microparticles with a desired particle size distribution (an average particle size of not more than about 400 μm, more particularly not more than about 300 μm).

In accordance with another aspect of the invention, the method of manufacturing orally disintegrating tablets, which disintegrate on contact with saliva in the buccal cavity forming a smooth, easy-to swallow suspension with acceptable aftertaste, comprising taste-masked microparticles, which rapidly release the dose on entry into the stomach, is provided. The method, in accordance with this aspect of the invention, comprises the following steps:

a) preparing a drug containing core particle (crystal, bead, pellet or granule) by (i) drug-layering on an inert particle (e.g., a 50-100 mesh sugar sphere or cellulose sphere, such as Celphere® CP-203) from a solution/suspension comprising a polymeric binder and the drug in a fluid bed coater and applying a seal-coat of Opadry® Clear, or (ii) granulating the drug and a diluent/filler such as lactose, mannitol or microcrystalline cellulose with a polymeric binder, or (iii) granulating as above, followed by extrusion and spheronization;

b) coating drug containing core particles with a solution of a functional polymer blend comprising a water insoluble polymer and a gastrosoluble polymer to produce effectively taste-masked microparticles with a desired particle size distribution (an average particle size of not more than about 400 μm, more particularly not more than about 300 μm);

c) granulating a sugar alcohol or a saccharide, or a combination thereof, each of which has an average particle diameter of not more than about 30 μm, with a disintegrant such as Crospovidone using water or an alcohol-water mixture in a typical granulator and drying in fluid bed equipment to produce rapidly-dispersing microgranules with an average particle size not more than about 400 μm (typically with an average particle size of not more than about 300 μm);

d) blending taste-masked microparticles of step (b) with rapidly disintegrating microgranules of step (c) at a ratio of from about 1/6 to 1/1 more particularly from about 1/4 to 1/2, and optionally other acceptable ingredients such as a flavoring agent, a coloring agent, and a sweetener in sufficient quantities typically up to about 1%, more particularly about 0.5% and additional disintegrant up to about 5%, more particularly about 4% based on the tablet weight; and e) compressing into tablets using a conventional rotary tablet press equipped with an external lubrication system to pre-lubricate the dies and punches.

In Vitro Dissolution Testing:

The taste-masking property of the taste-masked microparticles and the orally disintegrating tablets in the mouth is evaluated by determining the percentage of drug-release (a release of not more than about 10% of the dose in about 3 minutes is considered acceptable) when tested for dissolution using USP Apparatus 1 (baskets @ 100 rpm) or Apparatus 2 (paddles @ 50 rpm) in 900 mL of simulating saliva fluid at a pH of about 6.8. Further, the rapid-release property in the stomach of the taste-masked microparticles and the orally disintegrating tablets is evaluated by determining the percentage of drug-release (a release of not less than about 60% of the dose in about 30 minutes is typically considered acceptable) when tested for dissolution using USP Apparatus 1 (baskets @ 100 rpm) in 900 mL of simulated gastric fluid or 0.1N HCl (at pH 1.2).

In accordance with certain embodiments of the invention, the taste-masked pharmaceutical composition is in the form of a tablet and exhibits low friability in order to be suitable for packaging blisters and bottles for storage, transportation and commercial distribution. Friability can be determined in accordance with the standard pharmaceutical test methods that are well known to those skilled in the art. Friability for tablets produced in accordance with certain aspects of the invention will have a friability of not more than about 1% and in accordance with certain embodiments not more than about 0.5%.

The following non-limiting examples illustrate the taste-masked microparticle composition or an orally disintegrating tablet dosage form comprising one or more therapeutic agent(s) requiring taste-masking, manufactured in accordance with the invention, which exhibits acceptable taste-masking when placed in the mouth and substantially complete, rapid-release of the dose on entry into the stomach. All percentages and ratios are by weight unless indicated otherwise.

Example 1

IR Beads (Drug Load: Approximately 16% Diphenhydramine Citrate):

Diphenhydramine citrate (293.4 g) was slowly added to an aqueous solution of 32.6 g polyvinylpyrrolidone (binder) and 978 g of purified water and mixed well. 60-80 mesh (177-250 micron) sugar spheres (1470 g) were coated with the drug-layering formulation in a Glatt fluid-bed coater equipped with a bottom-spray Wurster insert. The drug containing pellets were dried, and a seal coat of Opadry Clear for a weight gain of 2% was applied on the drug-layered beads.

Taste-Masked Beads (Drug Load: Approximately 12% Diphenhydramine Citrate at 25% Coating):

IR beads (1100 g) were coated with a solution of Ethocel/E100/plasticizer at a ratio of 46.3/46.3/7.4 dissolved in 98/2 acetone/water for a weight gain of up to 25%. The plasticizer used consisted of Imwitor 900 (2.78%) and triethyl citrate (4.62%). The coated beads were dried in the Glatt GPCG-3. The actual assay values of the beads coated at 15 and 25% by weight were 0.073 and 0.064%, respectively. These taste-masked beads released 12% (15% coated) and 8% (25% coated) in 5 minutes when dissolution tested using the USP Apparatus 2 (paddles @ 50 rpm in a phosphate buffer at pH 6.8).

Rapidly-Dispersing Microgranules:

The rapidly-dispersible microgranules comprising a sugar alcohol such as mannitol and a disintegrant such as crospovidone are prepared following the procedure disclosed in the co-pending U.S. patent application Ser. No. 10/827,106 filed Apr. 19, 2004. Currently, D-mannitol (147 kg) with an average particle size of approximately 20 μm or less (Pearlitol 25 from Roquette, France) is blended with 8 kg of cross-linked povidone (Crospovidone XL-10 from ISP) in a high shear granulator (GMX 600 from Vector) and granulated with an aqueous solution of 5 kg mannitol dissolved in 37 kg purified water. Two such high shear granulation batches are vacuum-transferred into a fluid-bed drier, Glatt GPCG 200 through a Comil from Quadro and dried in the Glatt. The rapidly-dispersible microgranules thus obtained typically have an average particle size in the range of approximately 125-200 μm.

ODT Diphenhydramine Citrate:

Taste-masked beads at 15% and 25% coating and the mix (93.38%, rapidly-dispersing microgranules, 5.91% crospovidone, 0.35% orange flavor, and 0.35% Aspartame) at a ratio of 1/3, were blended together and compressed into 441 mg (15% coating) or 500 mg (25% coating) tablets containing 20.3 mg of diphenhydramine citrate with an average hardness of 6 kP. The tablets released 13% and 3% in about 5 minutes, respectively, when dissolution tested using the USP Apparatus 2 (paddles @ 50 rpm) at pH 6.8. In contrast, almost complete release of the active in about 5 minutes was observed when dissolution tested in 0.1N HCl as illustrated in FIG. 1.

Example 2 (Comparative)

Drug-Layered Diphenhydramine Hydrochloride Beads (Drug Load: 15%):

Diphenhydramine hydrochloride (375 g) was slowly added to an aqueous solution of 41.8 g polyvinylpyrrolidone (binder) and 1667 g of purified water and mixed well. 60-80 mesh sugar spheres (1470 g) were coated with the drug-layering formulation in a Glatt GPCG 3. The drug containing pellets were dried, and a seal coat of Opadry Clear for a weight gain of 4% was applied on the drug-layered beads.

Reference Example: Taste-Masked Beads with Ethylcellulose (EC-10) Alone

Figure 2:
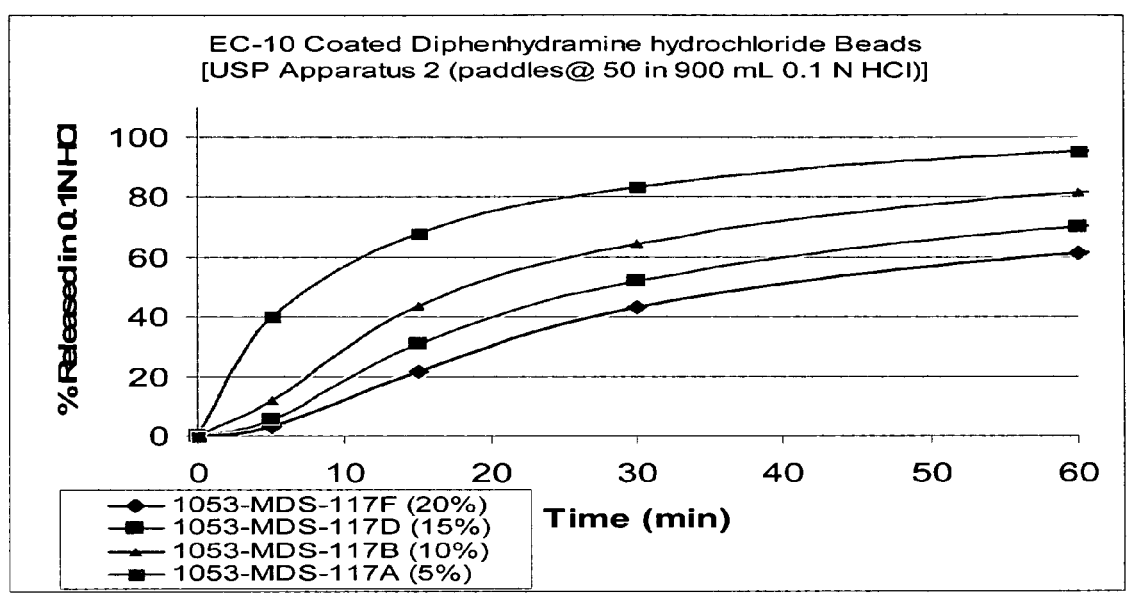
FIG. 2 illustrates the dissolution profiles in 0.1N HCl of taste-masked diphenhydramine hydrochloride beads of Example 2 (comparative)

IR beads were coated with a solution of EC-10/Myvacet 9-45 at a ratio of 90/10 dissolved in 95/5 acetone/water for a weight gain of up to 20%. The coated beads were dried in the Glatt GPCG-3. The taste-masked beads coated at 20% typically release less than about 10% in 5 minutes when dissolution tested using the USP Apparatus 2 (paddles @ 50 rpm in a phosphate buffer at pH 6.8). The dissolution profiles in 0.1N HCl of the beads with a membrane thickness of up to 20% by weight are shown in FIG. 2 suggesting that both taste-masking and rapid release cannot be achieved when coated with ethylcellulose alone.

Example 3

Taste-Masked Beads with Ethylcellulose/Eudragit E100 (Drug Load: Approximately 12% Diphenhydramine Hydrochloride):

IR beads produced in Example 2 would be coated with a solution of EC-10/E100 at a ratio of 46.3/46.3 with Myvacet 9-45/talc at 4.62/2.78 dissolved in 95/5 acetone/water for a weight gain of up to 20%. The coated beads would be dried in the Glatt GPCG-3. The taste-masked beads coated at 20% would release not more than about 15% in 5 minutes when dissolution tested using the USP Apparatus 2 (paddles @ 50 rpm in a phosphate buffer at pH 6.8). Yet the taste-masked beads would release not less than about 90% in 5 minutes when dissolution tested in 0.1N HCl, irrespective of the thickness of the membrane applied on the beads.

ODT Diphenhydramine Hydrochloride:

208 parts of taste-masked beads at 20% coating and 624 parts of the mix (93.38%, rapidly-dispersing microgranules, 5.91% crospovidone, 0.35% orange flavor, and 0.35% Aspartame) would be blended together and compressed into 832 mg tablets containing 25 mg of diphenhydramine hydrochloride with an average hardness of 6 kP. The tablets would release not more than 10% in about 5 minutes when dissolution tested using the USP Apparatus 2 (paddles @ 50 rpm) at pH 6.8. In contrast, almost complete release of the active in about 20 minutes was observed when dissolution tested in 0.1N HCl.

Example 4 (Comparative)

Reference Example: Taste-Masked Beads with Polyvinyl Acetate Alone (Drug Load: Approximately 12% Diphenhydramine Hydrochloride)

Figure 3:
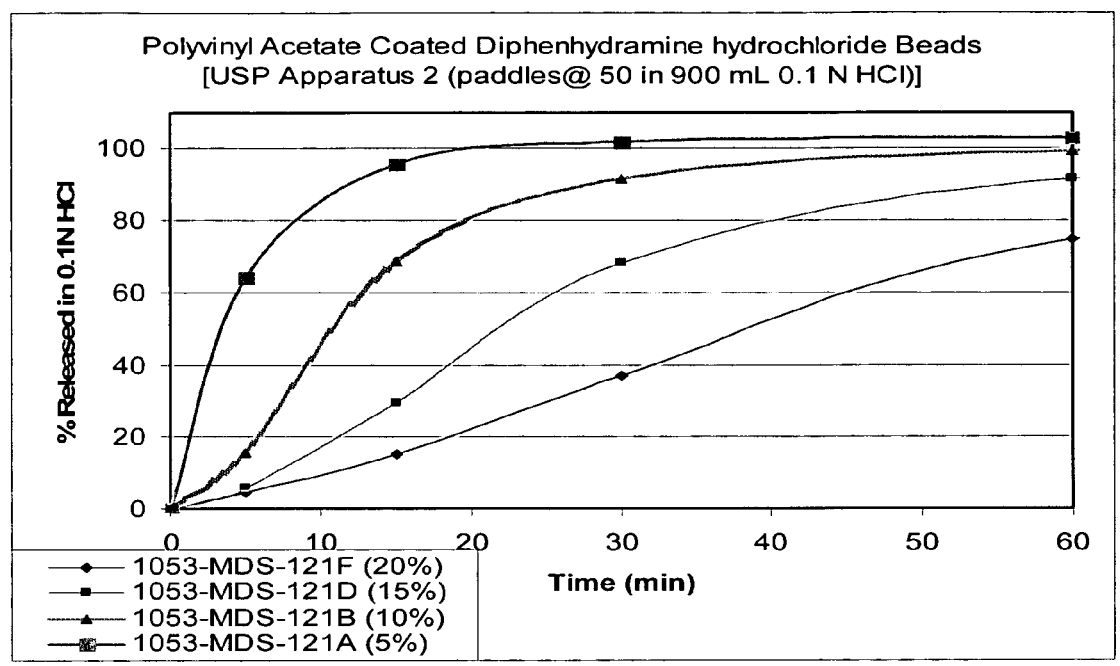
FIG. 3 illustrates the dissolution profiles in 0.1N HCl of taste-masked diphenhydramine hydrochloride beads of Example 4 (comparative)

IR beads produced in Example 2 were coated with a solution of polyvinyl acetate (Kolloidon SR30D) with Myvacet 9-45/talc at 2.9/11.5 dissolved in 87/13 ethanol/water for a weight gain of up to 20%. The coated beads were dried in the Glatt GPCG-3. The taste-masked beads coated at 20% typically release less than 10% in 5 minutes when dissolution tested using the USP Apparatus 2 (paddles @ 50 rpm in a phosphate buffer at pH 6.8). The dissolution profiles in 0.1N HCl of the beads with a membrane thickness of up to 20% by weight are shown in FIG. 3. Based on these observations as well as the observations in Example 2, it is amply clear that both effective taste-masking and rapid dissolution in acidic buffers cannot be achieved when coated with a water-insoluble polymer (e.g., ethylcellulose or polyvinyl acetate) alone.

Example 5

Taste-Masked Beads with Polyvinyl Acetate/Eudragit E100 (Drug Load: Approximately 12% Diphenhydramine Hydrochloride):

IR beads produced in Example 2 would be coated with a solution of polyvinyl acetate/Eudragit E100 at a ratio of 65/25 with Myvacet 9-45/talc at 6.5/3.5 dissolved in 90/10 ethanol/water for a weight gain of up to 20%. The coated beads would be dried in the Glatt GPCG-3. The taste-masked beads coated at 20% would release not more than 10% in 5 minutes when dissolution tested using the USP Apparatus 2 (paddles @ 50 rpm in a phosphate buffer at pH 6.8). Yet the taste-masked beads would release not less than 80% in 5 minutes when dissolution tested in 0.1N HCl, irrespective of the thickness of the membrane applied on the beads.

Example 6

Drug-Layered Cetirizine Dihydrochloride Beads (Drug Load: 8.4%):

Cetirizine dihydrochloride (180 g) was slowly added to an aqueous solution of 15.7 g polyvinylpyrrolidone (binder) and 782.8 g of purified water and mixed well. 60-80 mesh sugar spheres (1900 g) were coated with the drug-layering formulation in a Glatt GPCG 3. The drug containing pellets were dried, and a seal coat of Opadry Clear for a weight gain of 2% was applied on the drug-layered beads.

Figure 4:
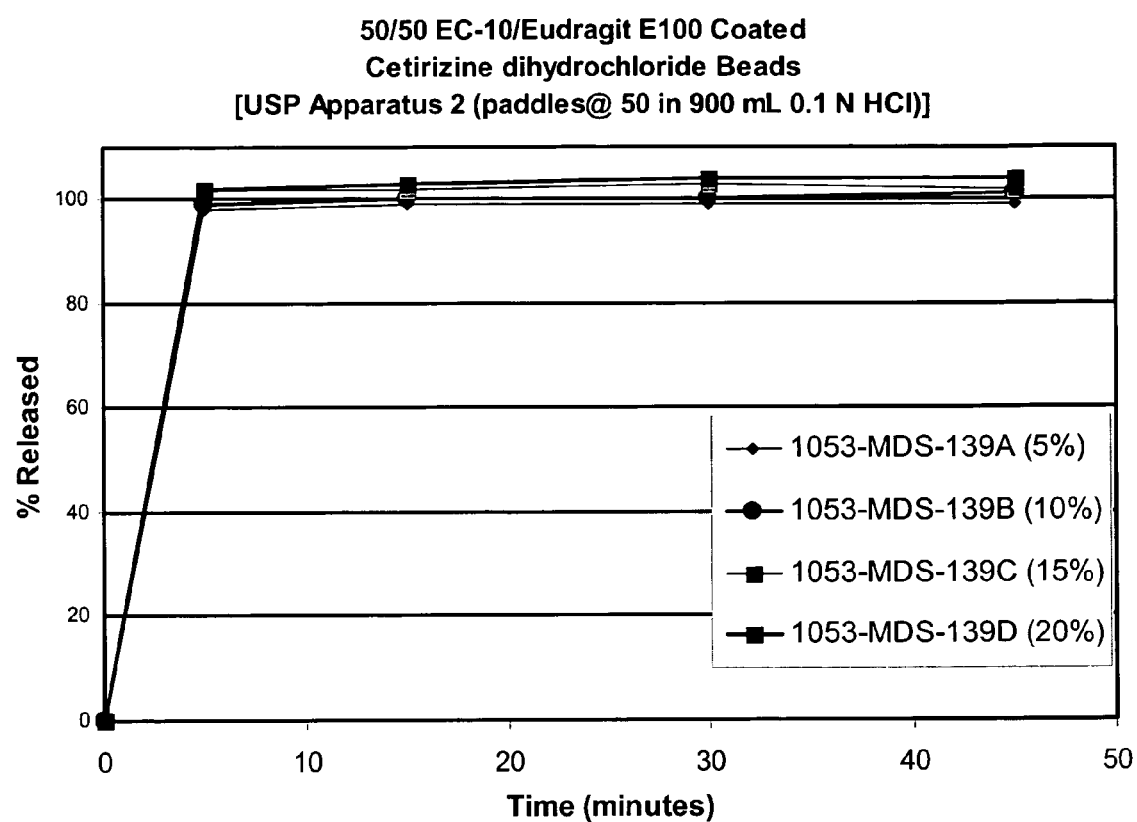
FIG. 4 illustrates the dissolution profiles in 0.1N HCl of taste-masked diphenhydramine hydrochloride beads of Example 6.

Taste-Masked Beads with Ethylcellulose/Eudragit E100:

IR beads were coated with a solution of EC-10/E100 at a ratio of 46.3/46.3 with Myvacet 9-45/talc at a ratio of 4.62/2.78 dissolved in 95/5 acetone/water for a weight gain of up to 20%. The coated beads were dried in the Glatt GPCG-3. The taste-masked beads coated at 20% released 13% in 5 minutes when dissolution tested using the USP Apparatus 2 (paddles @ 50 rpm in a phosphate buffer at pH 6.8). The dissolution profiles in 0.1N HCl of the beads with a membrane thickness of 5%, 10%, 15% and 20% by weight are shown in FIG. 4.

ODT Cetirizine Dihydrochloride:

744 g of taste-masked beads at 20% coating, 1734 g of rapidly-dispersing microgranules, 110 g of crospovidone, 13 g orange flavor, and 13 g of Aspartame) would be blended together and compressed into 520 mg tablets containing 10 mg of cetirizine dihydrochloride with an average hardness of 5 kP. The tablets would release not more than 10% in about 5 minutes when dissolution tested using the USP Apparatus 2 (paddles @ 50 rpm) at pH 6.8. In contrast, almost complete release of the active in about 20 minutes was observed when dissolution tested in 0.1N HCl.

Example 7

Taste-Masked Microparticles of Sumatriptan Succinate (Drug Load: Approximately 63% of Sumatriptan Succinate):

Sumatriptan succinate (90%) was granulated with an aqueous solution (25% solids) of hydroxypropyl methylcellulose (Methocel K100LV at 10% by weight of the drug) in a high-shear granulator and tray-dried in a convection oven. The resilient granules with an average particle size of about 200 μm would be coated with a 95/5 acetone/water solution (10% solids) containing 65/25 Ethocel (EC-10)/Eudragit E100 with TEC/talc at a ratio of 6.5/3.5 in a fluid-bed coater for a weight gain of up to 30%. The coated granules coated 30% would release less than 10% active in 5 minutes at pH 6.8. Yet the taste-masked beads would release not less than 80% in 5 minutes when dissolution tested in 0.1N HCl, irrespective of the thickness of the membrane applied on the beads.

Sumatriptan Succinate ODT (100 mg of Sumatriptan):

The taste-masked microparticles (720 g), rapidly-dispersing microgranules (6,150 g) and an orange flavor (40 g), Aspartame (80 g), iron oxide (30 g) and crospovidone (200 g) would be blended together and compressed into orally disintegrating tablets (average tablet weight of approximately 1 g and average hardness of 7.2 kP), using a rotary tablet press equipped with an external lubricating system. Sumatriptan Succinate ODT (100 mg as sumatriptan) would disintegrate in less than about 60 seconds in the oral cavity exhibiting a pleasant taste. The drug-release would be not more than about 10% in 5 minutes in the simulated saliva fluid (pH 6.8) and not less than about 85% in 30 minutes in 0.1N HCl.

Changes may be made by persons skilled in the art in the construction and the various components and assembly described herein or in the steps or the sequence of steps of the method of manufacture described therein without departing from the spirit and scope of the invention as described herein:

What is claimed is:

1. A pharmaceutical composition comprising:
   (1) a plurality of taste-masked particles, wherein each taste-masked particle comprises:
      (a) a drug-containing core particle;
      (b) a taste-masking membrane disposed on said drug-containing core particle comprising a combination of a water-insoluble polymer and a gastrosoluble polymer, wherein the water-insoluble polymer is selected from the group consisting of ethylcellulose, polyvinyl acetate, cellulose acetate, cellulose acetate phthalate, cellulose acetate butyrate, methacrylate copolymers and combinations thereof, and the gastrosoluble polymer is selected from the group consisting of maltodextrin, aminoalkyl methacrylate copolymer, polyvinylacetate diethylaminoacetate, and combinations thereof; wherein the ratio of the water-insoluble polymer to the gastrosoluble polymer in the taste-masking membrane ranges from about 95/5 to about 65/35 and the pharmaceutical composition releases greater than or equal to about 60% of the total amount of drug in 30 minutes when tested for dissolution using United States Pharmacopoeia Apparatus 2 using paddles at 50 rpm in 900 mL of pH 1.2 buffer; and wherein said taste-masked particles release not more than about 10% of the total amount of drug in about 3 minutes when dissolution tested in simulated saliva fluid at pH about 6.8; and
   (2) a plurality of rapidly-dispersing microgranules having an average particle size of not more than about 400 μm comprising (i) a disintegrant and (ii) a sugar alcohol or a saccharide or a combination thereof, wherein each of said disintegrant and sugar alcohol or saccharide is present in the form of particles having an average particle diameter of not more than about 30 μm, and wherein the pharmaceutical composition is an orally disintegrating tablet.

2. The pharmaceutical composition of claim 1 comprising one or more drug(s) present in sufficient quantities to be administered orally to a patient in need thereof at a prescribed dosing regimen to provide therapeutic efficacy.

3. The pharmaceutical composition of claim 1 wherein the drug-containing particle comprises a drug-layered bead comprising an inert particle coated with one or more pharmaceutically acceptable drug(s).

4. The pharmaceutical composition of claim 1, wherein the drug-containing particle comprises a microgranule or an extruded and spheronized pellet, wherein the microgranule or pellet comprises (1) one or more pharmaceutically acceptable drug(s), (2) a polymeric binder, and (3) a filler and/or diluent.

5. The pharmaceutical composition of claim 1, wherein said drug requires taste-masking.

6. The pharmaceutical composition of claim 1, wherein the drug is selected from the group consisting of diphenhydramine, ranitidine, cimetidine, famotidine, astemizole, cetirizine, fexofenadine, omeprazole, lansoprazole, sumatriptan, rezitriptan, eletriptan, zolmitriptan, ondansetron, granisetron, clonazepam, tiagabine, tizanidine, zolpidem, zaleplon, zafirlukast, montelukast, sildenafil, tadalafil, pharmaceutically acceptable salts thereof, and combinations thereof.

7. The pharmaceutical composition of claim 1 wherein the membrane thickness ranges from about 5% to 50% by weight of the coated particle.

8. The pharmaceutical composition of claim 1 wherein the water-insoluble polymer comprises ethylcellulose and the gastrosoluble polymer comprises an aminoalkyl methacrylate copolymer.

9. The pharmaceutical composition of claim 1 wherein the sugar alcohol or saccharide to disintegrant ratio is from about 90/10 to about 99/1.

10. The pharmaceutical composition of claim 1, wherein the ratio of rapidly-dispersing microgranules to taste-masked particles ranges from about 6/1 to about 2/1.

11. The pharmaceutical composition of claim 1 wherein the rapidly-dispersing microgranules comprise a disintegrant selected from the group consisting of crosslinked polyvinylpyrrolidone, sodium starch glycolate, crosslinked sodium carboxymethylcellulose, low-substituted hydroxypropylcellulose and mixtures thereof.

12. The pharmaceutical composition of claim 1, wherein the average particle size of the drug-containing core particle is not more than about 400 μM.

13. The pharmaceutical composition of claim 1, wherein said orally disintegrating tablet has a friability of not more than about 1%.

14. The pharmaceutical composition of claim 1, wherein said orally disintegrating tablet disintegrates on contact with the saliva in the oral cavity within approximately 60 seconds.

15. The pharmaceutical composition of claim 1, wherein the rapidly dispersing microgranules comprise a sugar alcohol or a saccharide selected from the group consisting of mannitol, xylitol, sorbitol, maltol, maltitol, lactose, sucrose, maltose, and combinations thereof.

16. The pharmaceutical composition of claim 1, wherein the pharmaceutical composition exhibits acceptable taste-masking when placed in the oral cavity for 60 seconds.

17. The pharmaceutical composition of claim 1, wherein the rapidly dispersing microgranules have an average particle size of not more than 300 μm.

18. The pharmaceutical composition of claim 1, wherein the ratio of the water-insoluble polymer to the gastrosoluble polymer in the taste-masking membrane ranges from about 85/15 to about 65/35.

19. A method of manufacturing a pharmaceutical composition comprising:
(a) preparing core particles comprising a drug; and
(b) coating the core particles by applying a membrane comprising a mixture of water-insoluble polymer and a gastrosoluble polymer wherein the water-insoluble polymer is selected from the group consisting of ethylcellulose, polyvinyl acetate, cellulose acetate, cellulose acetate phthalate, cellulose acetate butyrate, methacrylate copolymers and combinations thereof and the gastrosoluble polymer is selected from the group consisting of maltodextrin, aminoalkyl methacrylate copolymer, polyvinylacetate diethylaminoacetate, and combinations thereof; wherein the ratio of the water-insoluble polymer to the gastrosoluble polymer in the taste-masking membrane ranges from about 95/5 to about 65/35;
(c) granulating particles of a sugar alcohol and/or a saccharide, each particle of sugar alcohol and/or saccharide having an average particle diameter of not more than 30 μm, with a disintegrant having an average particle diameter of not more than 30 μm to produce rapidly-dispersing microgranules with an average particle size of not more than about 400 μm;
(d) blending the membrane coated microparticles of step (b) with the rapidly-dispersing microgranules of step (c) at a ratio of about ⅙ to about ½; and
(e) compressing the blend of step (d) into orally disintegrating tablets.

20. The method of claim 19 wherein the water-insoluble polymer comprises ethylcellulose and the gastrosoluble polymer comprises an aminoalkyl methacrylate copolymer.

21. The method of claim 19, wherein said step of compressing (e) comprises utilizing a conventional rotary tablet press equipped with an external lubrication system to pre-lubricate the dies and punches.

22. The method of claim 19, wherein the orally disintegrating tablet, when tested for dissolution using United States Pharmacopoeia Apparatus 2 using paddles at 50 rpm in 900 mL buffer, release not more than about 10% of the total amount of the drug in about 3 minutes in a simulated saliva buffer at pH 6.8 and greater than or equal to about 60% of the total amount of the drug in about 30 minutes in an acidic buffer at pH 1.2.

23. The method of claim 19 wherein said rapidly-dispersing microgranules have an average particle size of not more than 300 μm.

24. The method of claim 19, wherein the membrane is present in an amount of from about 5% to about 50% based on the total weight of the coated particles.

25. The method of claim 19, wherein the pharmaceutical composition exhibits acceptable taste-masking when the composition is placed in the oral cavity for 60 seconds.

26. The method of claim 19, wherein the pharmaceutical composition releases not less than about 60% of the total amount of the drug in 30 minutes when tested for dissolution using United States Pharmacopeia Apparatus 2 using paddles at 50 rpm in 900 mL of pH 1.2 buffer.

27. The method of claim 19, wherein the ratio of the water-insoluble polymer to the gastrosoluble polymer in the taste-masking membrane ranges from about 85/15 to about 65/35.

* * * * *

UNITED STATES PATENT AND TRADEMARK OFFICE
CERTIFICATE OF CORRECTION

PATENT NO. : 9,884,014 B2  
APPLICATION NO. : 11/248596  
DATED : February 6, 2018  
INVENTOR(S) : Gopi M. Venkatesh Page 1 of 1

It is certified that error appears in the above-identified patent and that said Letters Patent is hereby corrected as shown below:

In the Claims

Column 16, Line 12, Claim 1 'pH 1.2 buffer' should read --0.1 N HCl at pH 1.2--.

Column 18, Line 26, Claim 22 'an acidic buffer at pH 1.2' should read --0.1 N HCl at pH 1.2--.

Column 18, Line 41, Claim 26 'pH 1.2 buffer' should read --0.1 N HCl at pH 1.2--.

Signed and Sealed this
Twenty-fifth Day of September, 2018

Andrei Iancu
*Director of the United States Patent and Trademark Office*